United States Patent [19]

Hirano et al.

[11] 3,973,036

[45] Aug. 3, 1976

[54] CYCLOPROPANECARBOXYLIC ACID ESTERS

[75] Inventors: Masachika Hirano, Ashiya; Takashi Matsuo, Nishinomiya; Hisami Takeda; Toshio Nishioka, both of Takarazuka, all of Japan

[73] Assignee: Sumitomo Chemical Company, Limited, Osaka, Japan

[22] Filed: Oct. 6, 1975

[21] Appl. No.: 620,188

[30] Foreign Application Priority Data

Oct. 24, 1974  Japan............................... 49-123244

[52] U.S. Cl............................ 424/304; 260/465 D; 260/465 F; 260/468 H; 424/305
[51] Int. Cl.[2] ..................... A01N 9/20; A01N 9/24; C07C 69/74; C07C 121/75
[58] Field of Search.................. 260/465 D, 468 H; 424/304, 306, 305

[56] References Cited
UNITED STATES PATENTS

| | | | |
|---|---|---|---|
| 3,666,789 | 5/1972 | Itava et al............................ | 260/468 |
| 3,835,176 | 9/1974 | Matsuo et al...................... | 260/465 |

*Primary Examiner*—Lewis Gotts
*Assistant Examiner*—Dolph H. Torrence
*Attorney, Agent, or Firm*—Stevens, Davis, Miller & Mosher

[57] ABSTRACT

A novel cyclopropanecarboxylic acid ester of the formula,

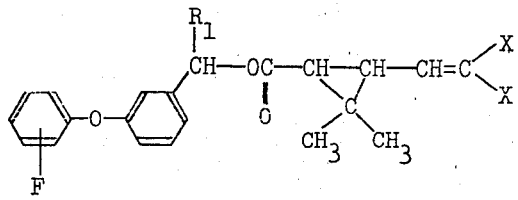

wherein $R_1$ is a hydrogen atom, a cyano or ethynyl group, and X is a chlorine, bromine or fluorine atom, which possesses various useful insecticidal and acaricidal activities and can be prepared by reacting a compound of the formula,

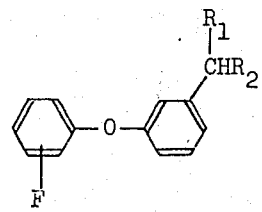

wherein $R_1$ is as defined above and $R_2$ is hydroxyl, a halogen atom or an arylsulfoxy group, with a cyclopropanecarboxylic acid of the formula,

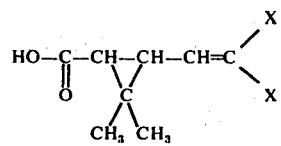

wherein X is as defined above, or its reactive derivative.

7 Claims, No Drawings

3,973,036

CYCLOPROPANECARBOXYLIC ACID ESTERS

The present invention relates to a novel cyclopropanecarboxylic acid ester of the formula,

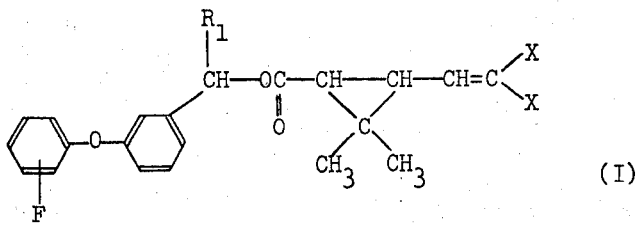

(I)

wherein $R_1$ is a hydrogen atom, a cyano or ethynyl group, and X is a chlorine, bromine or fluorine atom, which is useful as an insecticide and acaricide. An object of the present invention is to provide an insecticide and an acaricide, at a low cost, which have low-toxicity to mammals but have a strong insecticidal activity for use in agriculture and horticulture as well as public health.

Among the insecticides which are now in common use, those which have an immediate effect upon insects, are harmless to mammals and therefore can be used without anxiety, are pyrethrum extracts (containing pyrethrin) and synthetic allethrin which is a homologue of the active ingredient of the extracts. However, the pyrethrum extracts tend to be limited in use owing to the relatively high cost in spite of the excellent usefulness.

The inventors synthesized various cyclopropanecarboxylic acid esters and tested the biological activity thereof. As the result, it was found that the esters of the formula (I) have an excellent insecticidal activity against sanitary insects such as houseflies and the like, particularly against insects injurious to agriculture such as green rice leafhoppers, diamond-back moths, armyworms, cutworms and the like, and also against mites. The inventors further found that the esters have low toxicity to mammals and can be prepared at a relatively low cost.

The esters of the present invention can be widely used for public health and further they are also so superior in the insecticidal activity against insects injurious to stored cereals, agriculture or forestry that they are very useful for controlling these insects. Particularly, they are so low in toxicity that they can be used for agricultural crops before harvest, green-house cultivation, household horticulture and food-packaging.

The novel cyclopropanecarboxylic acid esters of formula (I) are prepared by reacting a compound of the formula (II),

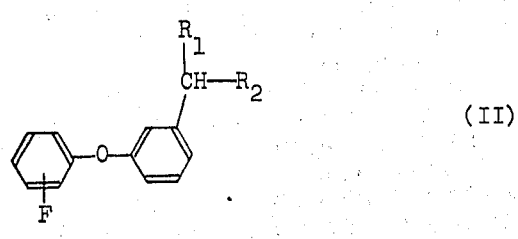

(II)

wherein $R_1$ is a hydrogen atom, a cyano or ethynyl group and $R_2$ is a hydroxyl, a halogen atom or an arylsulfoxy group, with a cyclopropanecarboxylic acid of the formula (III),

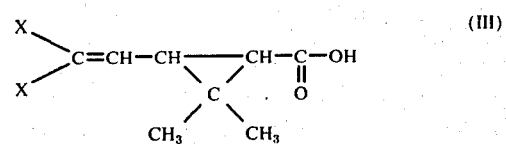

(III)

wherein X is a chlorine, bromine or fluorine atom, or its reactive derivative, if necessary, in the presence of suitable solvents, reaction auxiliaries and catalysts.

The compound of the formula (II) includes the reactive derivatives of the alcohol which are obtained by substituting the hydroxyl group of the alcohol with a halogen atom or a tosyloxy group. The reactive derivatives of the cyclopropanecarboxylic acid of the formula (III) include acid halides, acid anhydrides, lower alkyl esters, alkali metal salts and the like.

The esters represented by the formula (I) include geometrical isomers owing to the steric configuration of the carboxylic acid (III) and optical isomers owing to the asymmetric carbon atoms of the alcohol (II) and carboxylic acid (III). It is a matter of course that the present invention includes all these isomeric esters.

In carrying out the process of the present invention an alcohol of the formula (II) is reacted with a carboxylic acid of the formula (III) or its acid halide, acid anhydride or lower alkyl ester. When the carboxylic acid is used, the reaction is achieved under conditions of dehydration by reacting the compound of the formula (II) in the form of an alcohol with the carboxylic acid of the formula (III) under heating in the presence of acid catalysts such as mineral acids, p-toluenesulfonic acid and the like, and azeotropic solvents such as benzene, toluene and the like. The reaction may also be well achieved by reacting the corresponding alcohol and acid, at room temperature or under heating, in inert solvents such as benzene and petroleum ether in the presence of dehydrating agents such as dicyclohexylcarbodiimide.

When the carboxylic acid halide is used, the reaction is sufficiently achieved at room temperature by reacting the alcohol of the formula (II) with the acid halide using organic tertiary bases such as pyridine, triethylamine and the like as a dehydrohalogenating agent. The acid halide used for this purpose may optionally be selected in the present invention, but acid chloride is usually used. in this reaction, the presence of solvents is desirable for smooth progress of the reaction and an inert solvent such as benzene, toluene, petroleum benzine or the like is usually used.

When the carboxylic acid anhydride is used, the reaction can be achieved by reacting the alcohol of the formula (II) with the acid anhydride at room temperature without particular reaction auxiliaries. In this reaction, heating of the reaction system and use of inert solvents are desirable for smooth progress of the reaction, but they are not essential.

When the lower alkyl ester of the carboxylic acid is used, the reaction is achieved by heating the reaction system in the presence of a basic catalyst such as sodium ethoxide or the like, and use of an inert solvent such as benzene, toluene or the like is desirable for smooth progress of the reaction. The preferred lower alkyl esters used herein include methyl ester, ethyl ester, n-propyl ester, isopropyl ester and n-butyl ester.

Alternatively, the esters of the formula (I) may be prepared by reacting the compound of the formula (II) in the form of a halide or an arylsulfonate with an alkali metal salt or an organic tertiary base salt of the carboxylic acid of the formula (III). The halide used herein is a chloride or bromide in general but other halides can also be used optionally, Alternatively, bases which can form these salts may be added to the reaction system together with the carboxylic acid. In this reaction, it is desirable for performance of the reaction to use inert solvent such as benzene and acetone and to heat the solvent at the boiling point or lower.

Referring to carboxylic acids of formula (III) used in the methods of this invention, the acid wherein X is a chlorine atom is disclosed in J. Farkas, et. al., Chem. listy 52, 688 (1958) [C.A. 52, 13650 (1958)] and the literature reports that the allethrolone ester of the carboxylic acid has an efficacy closely similar to that of the ester of chrysanthemic acid. This acid is easily obtained from low-priced materials such as chloral and isobutene. Furthermore, reactive derivatives of this carboxylic acid can easily be obtained from the acid by the well-known methods, for example, by applying to the chrysanthemic acid.

The compound of the formula (II) in the form of a halide or an arylsulfonate is easily obtained by halogenating the compound of the formula (II) in the form of an alcohol, or by reacting the alcohol of formula (II) with p-toluenesulfonic acid chloride or the like.

The standard methods of the invention will be illustrated with reference to the following examples A to F, as shown below.

A. Method by the reaction between the alcohol and the carboxylic acid halide

The alcohol (0.05 mole) is dissolved in a dry benzene of three times the volume of the alcohol, and 0.075 mole of pyridine is added to the solution. Separately, 0.053 mole of the carboxylic acid chloride is dissolved in dry benzene of three times the volume of the acid chloride, and the resulting solution is added at one time to the former solution. The reaction proceeds with generation of heat. The reaction solution is allowed to stand overnight after sealing the reaction vessel tightly. Thereafter, a small amount of water is added thereto to dissolve deposited pyridine hydrochloride and the aqueous layer is separated. The organic layer obtained is washed successively with a 5% aqueous hydrochloric acid solution, a saturated aqueous sodium hydrogen carbonate solution and then a saturated aqueous sodium chloride solution. After drying over anhydrous sodium sulfate, benzene is removed under reduced pressure and the residue obtained is purified by chromatography over silica gel to obtain the objective ester.

B. Method by the dehydration reaction between the alcohol and the carboxylic acid The alcohol (0.05 mole) and the carboxylic acid (0.05 mole) are dissolved in each benzene of three times the volume of the reactants. To the solution is added 0.08 mole of dicyclohexylcarbodiimide, and the mixture is allowed to stand overnight after sealing the reaction vessel tightly. On the next day, the reaction is completed by refluxing the solution for two hours, and then the objective compound is obtained by the same after-treatment as described in the method A.

C. Method by the reaction between the alcohol and the carboxylic acid anhydride

The alcohol (0.05 mole) is dissolved in toluene of three times the volume of the alcohol and 0.05 mole of the carboxylic acid anhydride (prepared from the carboxylic acid and acetic anhydride) is added thereto. The mixture is reacted at 100°C for 3 hours under heating and then cooled. The reaction solution is neutralized with a 10% aqueous sodium hydroxide solution at 10°C or below and the carboxylic acid which was produced by the reaction is recovered as sodium salt. Thereafter the organic layer is treated in the same manner as described in the method A to obtain the objective ester.

D. Method by the ester-exchange reaction between the alcohol and the lower alkyl ester of the carboxylic acid The alcohol (0.05 mole) and the carboxylic acid ethyl ester (0.05 mole) are dissolved together in dry toluene of five times the volume of them, and 0.005 mole of sodium ethoxide is added thereto. The mixture is heated under reflux during which ethanol produced with progress of the reaction is removed as the azeotropic mixture with the solvent using a rectifying column. Thereafter cold water is added thereto and the solution is separated into layers. The objective compound is obtained by the same aftertreatment as described in the method A.

E. Method by the reaction between the halide and the carboxylic acid

The halide (0.05 mole) and the carboxylic acid (0.06 mole) are dissolved in acetone of three times the volume of them. The resulting solution is kept at 15° to 20°C, and a solution of 0.08 mole of triethylamine in acetone of three times the volume of the triethylamine is gradually added dropwise to the solution with stirring. After the dropwise addition is completed, the solution is refluxed for 2 hours to complete the reaction and then cooled. The deposited triethylamine hydrochloride is filtered out and the filtrate is freed of the acetone under reduced pressure. To the residual solution is added benzene of three times the volume of the solution and then the same after-treatment as described in the method A is carried out to obtain the objective ester.

F. Method by the reaction between the arylsulfonate and the carboxylic acid salt The arylsulfonate (0.05 mole) is dissolved in acetone of three times the volume of the arylsulfonate and 0.06 mole of the sodium carboxylate (prepared by reacting equimolar amounts of the carboxylic acid and sodium hydroxide in water and removing water to dryness) is gradually added to the solution at room temperature with stirring. After the addition, the mixture is refluxed for 30 minutes to complete the reaction. After cooling, the deposited solid matter is filtered out and the filtrate is freed of the acetone under reduced pressure. The residue is dissolved in benzene of three times the volume of the residue and then the same after-treatment as described in the method A is carried out to obtain the objective compound.

elementary analysis column mean calculated value and found value, respectively.

Table 1

| Example No. | Alcohol or its derivative | Carboxylic acid or its derivative | Method |
|---|---|---|---|
| 1 | 3-(4-fluorophenoxy)-benzyl alcohol | acid chloride | A |
| 2 | 3-(3-fluorophenoxy)-benzylbromide | sodium carboxylate | E |
| 3 | 3-(4-fluorophenoxy)-α-cyano-benzyl alcohol | acid chloride | A |
| 4 | 3-(2-fluorophenoxy)-α-ethynyl-benzyl alcohol | acid chloride | A |
| 5 | 3-(4-fluorophenoxy)-benzyltosylate | sodium carboxylate | F |
| 6 | 3-(4-fluorophenoxy)-benzyl alcohol | 2,2-dimethyl-3-($\beta,\beta$-dibromovinyl)-cyclopropane-1-carboxylic acid chloride | A |
| 7 | 3-(4-fluorophenoxy)-α-cyano-benzyl alcohol | sodium 2,2-dimethyl-3-($\beta,\beta$dibromovinyl)-cyclopropane-1-carboxylate | E |
| 8 | 3-(4-fluorophenoxy)-benzyl alcohol | 2,2-dimethyl-3-($\beta,\beta$-difluorovinyl)-cyclopropane-1-carboxylic chloride | A |

| Compound No. | Esters obtained Name | Yield (%) | Refractive index | Elementary C(%) | analysis H(%) |
|---|---|---|---|---|---|
| (1) | 3-(4-fluorophenoxy)-benzyl 2',2'-dimethyl-3'-($\beta,\beta$-dichlorovinyl)-cyclopropane-1'-carboxylate | 96 | $n_D^{20}$ 1.5582 | (F) 61.26 (C) 61.62 | 4.61 4.68 |
| (2) | 3-(3-fluorophenoxy)-benzyl 2',2'-dimethyl-3'-($\beta,\beta$-dichlorovinyl)-cyclopropane-1'-carboxylate | 80 | $n_D^{24.5}$ 1.5564 | (F) 61.41 (C) 61.62 | 4.78 4.68 |
| (3) | 3-(4-fluorophenoxy)-α-cyano-benzyl 2',2'-dimethyl-3'-($\beta,\beta$-dichlorovinyl)-cyclopropane-1'-carboxylate | 95 | $n_D^{26.5}$ 1.5593 | (F) 61.02 (C) 60.85 | 4.14 4.17 |
| (4) | 3-(2-fluorophenoxy)-α-ethynylbenzyl 2',2'-dimethyl-3'-($\beta,\beta$-dichlorovinyl)-cyclopropane-1'-carboxylate | 96 | $n_D^{26.5}$ 1.5540 | (F) 63.52 (C) 63.74 | 4.38 4.42 |
| (1) | 3-(4-fluorophenoxy)-benzyl 2',2'-dimethyl-3'-($\beta,\beta$-dichlorovinyl)-cyclopropane-1'-carboxylate | 92 | $n_D^{27.5}$ 1.5560 | (F) 61.28 (C) 61.62 | 4.70 4.68 |
| (10) | 3-(4-fluorophenoxy)-benzyl 2',2'-dimethyl-3'-($\beta,\beta$-dibromovinyl)-cyclopropane-1'-carboxylate | 94 | $n_D^{25}$ 1.5631 | (F) 50.90 (C) 50.52 | 4.11 4.04 |
| (11) | 3-(4-fluorophenoxy)-α-cyanobenzyl 2',2'-dimethyl-3'-($\beta,\beta$-dibromovinyl)-cyclopropane-1'-carboxylate | 90 | $n_D^{25}$ 1.5649 | (F) 50.28 (C) 50.40 | 3.48 3.65 |
| (12) | 3-(4-fluorophenoxy)-benzyl 2',2'-dimethyl-3'($\beta,\beta$-difluorovinyl)-cyclopropane-1'-carboxylate | 95 | $n_D^{25}$ 1.5526 | (F) 67.09 (C) 66.83 | 5.30 5.34 |

The results obtained based on the abovementioned method A to F ae summarized in Table 1, but it is not to be interpreted as limiting the compounds of the invention thereto. The symbols (C) and (F) in the Examples of the compounds which are prepared in the same manner are given below, but the present invention is not limited to those compounds.

Compound No.

(5)

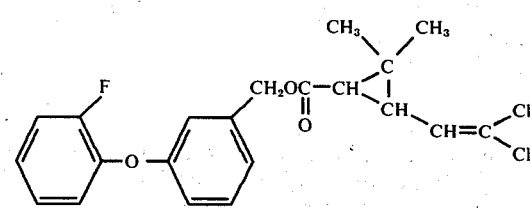

(6)

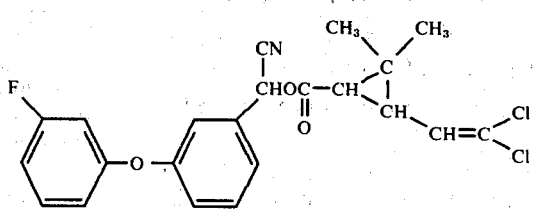

(7) 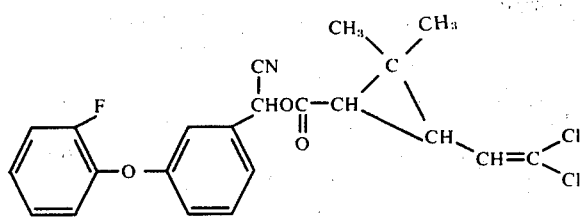

(8) 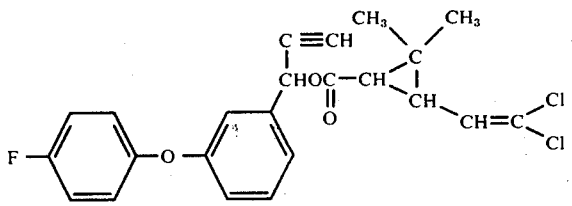

(9) 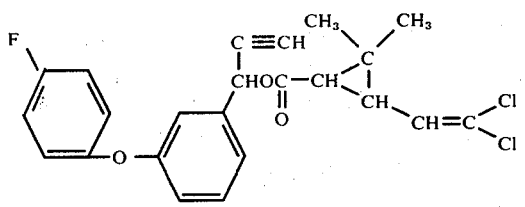

(13) 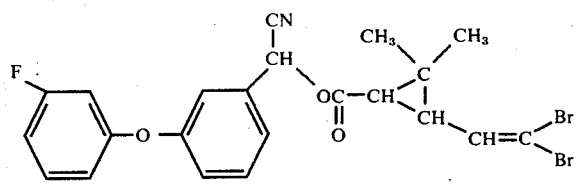

(14) 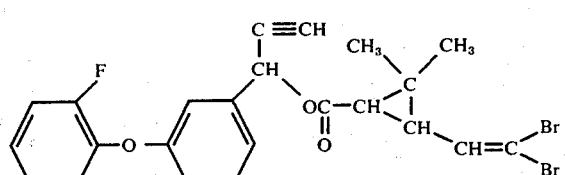

(15) 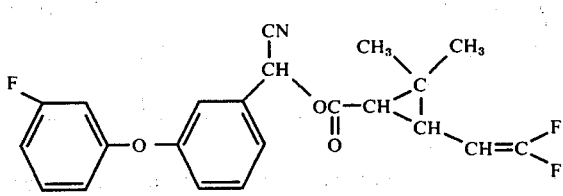

(16) 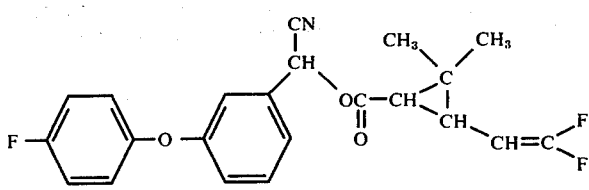

In order to demonstrate the effects of the present compounds more clearly, the experimental examples and their results will be shown with reference to the typical examples.

Experimental Example 1

Insecticidal activity on tobacco cut worm *Spodoptera litura*

Each of the present compounds (1), (2), (3), (5), (7), (11), (13) and (16) was formulated into a 20% emulsifiable concentrate according to the usual method. Further, 20% emulsifiable concentrates of the controls were also prepared.

Each 20% emulsifiable concentrate was diluted with water to a required test concentration. Ten milliliters of the diluted liquor were sprayed onto chinese cabbage grown up to a 3- to 4-leaves stage in a pot. After air-drying, the leaves were cut off and placed in a glass Petri dish of 14 cm in diameter and 7 cm in height, and 10 third instar larvae of tobacco cut worm (*Spodoptera litura*) were liberated therein. After 2 days, the dead and alive were counted and the values of $LC_{50}$ (50% lethal concentration) were obtained. The results obtained are as shown in Table 2.

Table 2

| Test compounds | LC$_{50}$ (ppm) | Relative efficacy (DDVP=100) |
| --- | --- | --- |
| Present compound (1) | 33 | 1363 |
| " (3) | 10 | 4500 |
| " (7) | 19 | 2368 |
| " (11) | 26 | 1730 |
| " (13) | 31 | 1451 |
| " (16) | 23 | 1956 |
| [structure: phenoxybenzyl ester of 2,2-dimethyl-3-(2,2-dichlorovinyl)cyclopropanecarboxylate type]* | 40 | 1125 |
| DDVP** | 450 | 100 |

\* Control: compound disclosed in Japanese Laid-Open No. 47531/1974
\** Control: 2,2-dichlorovinyl dimethyl phosphate

Experimental Example 2

Insecticidal activity on house-fly adults (*Musca domestica*)

Each of the present compounds (1), (2), (3), (5) and (6) was formulated into an oil spray of required test concentration with deodorized kerosene. In the same manner, the control compound, pyrethrin, was formulated into an oil spray.

Five milliliters of each oil spray were sprayed, using the Campbel's turn table apparatus [Soap and Sanitary Chemicals, Vol. 14, No. 119 (1938)]. Twenty seconds after spraying, the shutter was opened, and about 100 house-fly adults (*Musca domestica*) per group were exposed to the descending mist for 10 minutes and then transferred to a breeding cage. In the cage, the flies were fed and allowed to stand for one day at room temperature. Then the dead and alive were counted to obtain the mortality. The value of LC$_{50}$ of each compound was obtained from the mortality according to the Finney's method. The results obtained are as shown in Table 3.

Table 3

| Test compound | LC$_{50}$ (mg/ml) | Relative efficacy (pyrethrin = 100) |
| --- | --- | --- |
| Present compound (1) | 12 | 1833 |
| Present compound (2) | 11 | 2000 |
| Present compound (3) | 8 | 2750 |
| Present compound (5) | 25 | 880 |
| Present compound (6) | 7 | 3143 |
| Pyrethrin | 220 | 100 |

The present compounds can widely be used for controlling insects injurious to public health, such as, for example, houseflies, mosquitoes and cockroaches, and insects injurious to stored cereals, such as, for example, grain mite, indian meal moth and rice weevils. Moreover, the present compounds are extremely effective for controlling insects injurious to agriculture, horticulture and forestry, such as, for example, planthoppers, leafhoppers, army worms and cut worms, diamondback moth, tortorixes, aphids, stemborers, mites and Japanese giant silk moth; and animal-parasitic lyce and mites. The compounds can also be used for controlling a wide range of other harmful insects.

The insecticides and acaricides of the present invention not only cause the harmful insects to be knocked down and to die, but also they have repellency (the effect of keeping harmful insects away from their host plant). In particular, they are also very superior in that they can freely be used, due to their low toxicity and harmlessness to mammals, for agricultural crops before harvest, household horticulture, green-house cultivation and food-packaging.

In the practical application of the present compounds, they may be applied alone or in combination with a carrier for the convenience of use as a pesticide. The present compounds can be formulated into optional preparation forms without any special treating conditions according to the formulation of common pesticides. That is, the compounds are formulated into emulsifiable concentrates, wettable powders, dusts, granules, fine granules, oil sprays, aerosols, heating fumigants (mosquito coils, electric mosquito killers), thermal fogging agents, non-heating fumigants and baits by the methods well known to the skilled in the art, and they are used in the forms which are suitable for application methods and in combination with a carrier Furthermore, the insecticidal activity of the present compounds can be increased in combination with known synergists for pyrethroid such as α-[2-(2-butoxyethoxy)-ethoxy]-4,5-methylenedioxy-2-propyltoluene (hereinafter referred to as piperonylbutoxide), 1,2-methylenedioxy-4-[2-(octylsulfinyl)-propyl]-benzene (hereinafter referred to as sulfoxide), 4-(3,4-methylenedioxyphenyl)-5-methyl-1,3-dioxane (hereinafter referred to as sulfoxane), N-(2-ethylhexyl)-bicyclo[2,2,1]hepta-5-ene-2,3-dicarboximide (hereinafter referred to as MGK-264), octachlorodipropyl ether (hereinafter referred to as S-421) and isobornylthiocyano acetate (hereinafter referred to as Thanite); and with known synergists for allethrin or pyrethrin.

In general, the chrysanthemate type compounds tend to be inferior in the resistance to light, heat and oxidation. Accordingly, it is recommended to add to the compositions of the present invention a proper amount of stabilizing agents, for example, antioxidants or UV absorbers such as phenol derivatives including BHT and BHA, bisphenol derivatives, arylamine derivatives including phenyl-α-naphthylamine, phenyl-β-naphthylamine and condensation products of phenetidine and acetone, and benzophenone compounds.

Additionally, the present compounds can be formulated into multipurpose compositions having more superior activity in combination with other active ingredients such as allethrin, N-(chrysanthemoxymethyl)-3,4,5,6-tetrahydrophthalimide (hereinafter referred to as tetramethrin), 5-benzyl-3-furylmethylchrysanthemate (hereinafter referred to as Crysron (a registered trade mark of Sumitomo Chemical Co.)), 3-phenoxybenzyl chrysanthemate, 5-propargylfurfuryl chrysanthemate and 2-methyl-5-propargyl-3-furylmethyl chrysanthemate, including, for example d-trans- and d-cis, trans-chrysanthemic acid esters thereof, pyrethrum extracts, d-trans- or d-cis, transchrysanthemic acid esters of d-allethrolone, other well-known cyclopropanecarboxylic acid esters; organochlorine type insecticides, for example, DDT, BHC and methoxychlor; organophosphorus type insecticides such as, for example, O,O-dimethyl-0-(3-methyl-4-nitropheynl)-phosphorothioate (hereinafter referred to as Sumithion (a registered trade mark of Sumitomo Chemical Co.)), 0,0-dimethyl-0-4-cyanophenyl-phosphorothioate (hereinafter referred to as Cyanox (a registered trade mark of Sumitomo Chemical Co.)) and 0,0-dimethyl-0-(2,2-dichlorovinyl)-phosphate (hereinafter referred to as DDVP); carbamate type insecticides such as, for example, 1-naphthyl-N-methylcarbamate and 3,5-dimethylphenyl-N-methylcarbamate (hereinafter referred to as Meobal (a registered trade mark of Sumitomo Chemical Co.)); other insecticides or microbial insecticides such as for example, fungicides, nematocides, acaricides, and further herbicides, plant regulators, fertilizers, B.T. and B.M., insect hormone compounds, or other agricultural chemicals. Furthermore, a synergistic effect owing to the combination can also be expected.

Preparation of the present insecticidal and acaricidal composition and lethal effect thereof will be illustrated with reference to the following preparation examples and examples. All parts are by weight.

Preparation Example 1

0.1 part of each d-trans acid isomer of the present compounds (1), (2), (3), (4), (5), (6), (7), (8), (9), (10), (11), (12), (13), (14), (15) and (16) is dissolved in kerosene to provide a total weight of 100 parts. Thus oil sprays of each isomer are obtained.

Preparation Example 2

0.05 part of each dl-trans acid isomer of the present compounds (1), (2), (3), (4), (5), (6), (7), (8), (9), (10), (11), (12), (13), (14), (15) and (16), and 0.2 part of piperonyl-butoxide are dissolved in kerosene to provide a total weight of 100 parts. Thus oil sprays of each isomer are obtained.

Preparation Example 3

To 20 parts of each of the present compounds (1), (2), (3), (4), (5), (6), (7), (8), (9), (10), (11), (12), (13), (14), (15) and (16) are added 15 parts of Sorpol SM-200 (a registered trade mark of Toho Kagaku Co.) and 65 parts of xylene. The mixtures are each thoroughly mixed to make a solution. Thus emulsifiable concentrates of each compound are obtained.

Preparation Example 4

To 10 parts of each dl-trans acid isomer of the present compounds (1), (2), (3), (4), (5), (6), (7), (8),(9), (10), (11), (12), (13), (14), (15) and (16) are added 20 parts of S-421, 15 parts of Sorpol SM-200 (the same as above) and 55 parts of xylene. The mixtures are each thoroughly mixed to make a solution. Thus emulsifiable concentrates of each isomer are obtained.

Preparation Example 5

0.1 part of dl-trans acid isomer of the present compound (1), 0.2 part of tetramethrin, 7 parts of xylene and 7.7 parts of deodorized kerosene are mixed to make a solution. The solution is filled in an aerosol container. After attaching a valve portion to the container, 85 parts of propellant (liquefied petroleum gas) are charged therein under pressure through the valve. An aerosol is thus obtained.

Preparation Example 6

0.3 part of dl-trans acid isomer of the present compound (3), 0.1 part of d-trans isomer of Crysron (the same as above), 7 parts of xylene and 7.6 parts of deodorized kerosene are mixed to make a solution. The solution is filled in an aerosol container. After attaching a valve portion to the container, 85 parts of propellant (liquefied petroleum gas) are charged therein under pressure through the valve. An aerosol is thus obtained.

Preparation Example 7

0.2 part of d-trans acid isomer of the present compound (5), 0.1 part of Crysron (the same as above), 7 parts of xylene and 7.7 parts of deodorized kerosene are mixed to make a solution. The solution is filled in an aerosol container. After attaching a valve portion to the container, 85 parts of propellant (liquefied petroleum gas) are charged therein under pressure through the valve. An aerosol is thus obtained.

Preparation Example 8

0.3 g of each d-trans acid isomer of the present compounds (1), (2), (3) and (4), 0.3 g of allethrin and 0.6 g of BHT are dissolved in 20 ml of methanol. The solutions are each uniformly mixed with 98.8 g of a mosquito coil carrier containing Tabu powder, Pyrethrum marc and wood powder in a ratio of 3 : 5 : 1, and then the methanol is evaporated. To the residue obtained are added 150 ml of water and the mixture is kneaded thoroughly, shaped into a mosquito coil and dried. Thus mosquito coils of each isomer are obtained.

Preparation Example 9

0.15 g of each dltrans acid isomer of the present compounds (5), (6), (7), (8), (9), (10), (11), (12), (13), (14), (15) and (16), and 0.2 g of d-trans acid isomer of allethrin are dissolved in 20 ml of methanol. The solutions are each uniformly mixed with 99.65 g of a mosquito coil carrier (the same as above), and then the methanol is evaporated. To the residue obtained are added 150 ml of water and the mixture is kneaded thoroughly, shaped into a mosquito coil and dried. Thus a mosquito coils of each isomer are obtained.

Preparation Example 10

0.1 g of each dl-trans acid isomer of the present compounds (1) and (4), 0.1 g of BHT and 0.1 g of piperonyl-butoxide are dissolved in a suitable amount of chloroform. The solutions are each adsorbed uniformly on filter paper of 3.5 cm × 1.5 cm in size and 0.3 cm in thickness.

Thus, fibrous heating fumigant insecticidal compositions for use on a heater are obtained. Asbestos may be used as a fibrous carrier having the same effect, in place of pulp plate such as filter paper.

Preparation Example 11

0.02 g of each d-cis, trans acid isomer of the present compounds (2) and (5), 0.05 g of 5-propargylfurfuryl dl-cis, trans-chrysanthemate and 0.1 g of BHT are dissolved in a suitable amount of chloroform. The solutions are each absorbed uniformly on filter paper of 3.5 cm × 1.5 cm in size and 0.3 cm in thickness. Thus, fibrous heating fumigant insecticidal compositions for use on a heater are obtained.

Preparation Example 12

Twenty parts of each of the present compounds (1) and (2), 10 parts of Sumithion (the same as above) and 5 parts of Sorpol SM-200 (the same as above) are thoroughly mixed. The mixtures are each mixed with 65 parts of 300 mesh talc in a mortar while thoroughly stirring. Thus wettable powders of each compound are obtained.

Preparation Example 13

One part of each of the present compounds (1), (2), (3), (4), (5), (6), (7), (8), (9), (10), (11), (12), (13), (14), (15) and (16), and 2 parts of 1-naphthyl-N-methylcarbamate are dissolved in 20 parts of acetone, and then 97 parts of 300 mesh diatomaceous earth are added thereto. After thoroughly mixing in a mortar while stirring, acetone is removed by evaporation. Thus dusts of each compound are obtained.

Preparation Example 14

Three parts of each of the present compounds (1), (2), (3), (4), (5), (6), (7), (8), (9), (10), (11), (12), (13), (14), (15) and (16), 5 parts of Toyolignin CT (a registered trade mark of Toyo Spinning Co.) and 92 parts of GSM Clay (a registered trade mark of Zieklite Mining Co.) are thoroughly mixed in a mortar.

Then the mixtures are each mixed with water of 10% by weight based on the mixture, granulated by means of a granulator and air-dried. Thus granular preparations of each compound are obtained.

Preparation Example 15

Four parts of each of the present compounds (1) and (2), 2 parts of Cyanox (the same as above), 5 parts of Toyolignin CT (a registered trade mark of Toyo Spinning Co.) and 89 parts of GSM Clay (a registered trade mark of Zieklite Mining Co.) are thoroughly mixed in a mortar.

Then the mixtures are each mixed with water of 10% by weight based on the mixture, granulated by means of a granulator and air-dried. Thus fine granular preparations of each compound are obtained.

Preparation Example 16

0.1 part of d-trans acid isomer of the present compound (1), 0.2 part of d-trans acid isomer of allethrin, 11.7 parts of deodorized kerosene and 1 part of Atmos 300 (an emulsifier (a registered trade mark of Atlas Chemical Co.)) are thoroughly mixed and emulsified by an addition of 50 parts of distilled water. An aerosol container is then filled with the resulting emulsion and 35 parts of a 3 : 1 mixture of deodorized butane and deodorized propane. A water-based aerosol is thus obtained.

The insecticidal and acaricidal activities of the present compositions thus obtained are as follows.

EXAMPLE 1

Five milliliters of each of the oil sprays formulated by the Preparation examples 1 and 2 were sprayed, according to the Campbel's turn table method [Soap and Sanitray Chemicals, Vol. 14, No. 6, 119, (1938)]. About 100 house-fly adults (*Musca domestica*) per group were exposed to the descending mist for 10 minutes. By the next day, more than 80% of the flies were killed with each oil spray.

EXAMPLE 2

The emulsifiable concentrates formulated according to the Preparation Example 3 were each diluted 200,000 times with water. Two liters of each test emulsion so prepared were placed in a styrene case of 23 cm × 30 cm in area and 6 cm in depth, and about 100 full grown larvae of northern house mosquito (*Culex pipens pallens*) were liberated therein. By the next day, more than 90% of the larvae were killed with each concentrate.

EXAMPLE 3

In 1/50,000 Wagner pots were allowed to grow rice plants which had elapsed 45 days after sowing. The emulsifiable concentrates formulated according to the Preparation Example 3 were each diluted 200 times with water. Each test solution so prepared was individually sprayed on the rice plants in a proportion of 10 ml per pot. Each pot was covered with wire net and about 30 adults of green rice leafhoppers (*Nephotettix cincticeps*) were liberated in the pot. After one day, more than 90% of the leafhoppers were killed.

EXAMPLE 4

Each of the emulsifiable concentrates formulated according to the Preparation Example 4 was diluted 1,000 times with water. Ten larvae of diamond-back moth (*Plutella xylostella*) in the third to fourth instar stage were liberated in a glass Petri dish of 14 cm in diameter and 5 ml of each of the diluted liquors was sprayed from the spraying tower.

Thereafter, the larvae were liberated in another dish in which leaves of chinese cabbage had previously been placed. After two days, more than 90% of the larvae were killed with each concentrate.

EXAMPLE 5

The insecticidal activity on house-fly adults (*Musca domestica*) of the aerosols formulated according to the Preparation Examples 5, 6, 7 and 16 was tested by the aerosol test method (Soap and Chemical Specialities, Blue Book, 1965) using a (6 ft)$^3$ Peet Grady's chamber. Thus, with each aerosol, more than 80% of the flies were knocked down 15 minutes after spraying and more than 70% of the flies were killed by the next day.

EXAMPLE 6

About 50 northern house mosquito adults (*Culex pipiens pullens*) were liberated in a (70 cm)$^3$ glass chamber in which a battery-type small fan (wing diameter 13 cm) was placed and turned on. 0.1 Gram of each of the mosquito coils formulated according to the Preparation Examples 8 and 9 was ignited at one end and placed at the center of bottom of the chamber. With each mosquito coil, more than 90% of the adults were knocked down within 20 minutes and more than 80% of the adults were killed by the next day.

EXAMPLE 7

About 50 house-fly adults (*Musca domestica*) were liberated in a (70 cm)³ glass chamber in which a battery-type small fan (wing diameter 13 cm) was placed and turned on. Each of heating fumigant compositions formulated according to the Preparation Examples 10 and 11 was placed on a heater in the chamber and fumigated. More than 90% of the adults were knocked down within 20 minutes with each fumigant.

EXAMPLE 8

About 20 rice plants were grown up to a 3- to 4-leaves stage in a flower pot of 10 cm in diameter, and then a 1,000-fold aqueous dilute solution of each wettable powder formulated according to the Preparation Example 12 was applied thereto by means of a turn table. After air-drying, each pot was covered with a wire cage and 20 to 30 smaller brown planthopper adults (*Laodelphax striatellus*) were liberated therein. The dead and alive after 24 hours were counted and more than 80% of the mortality was obtained.

EXAMPLE 9

A glass Petri dish of 14 cm in diameter was coated on the inside wall with butter, leaving at the lower part an uncoated portion of 1 cm in height. Onto the bottom of the dish, each of the dusts formulated according to the Preparation Example 13 was uniformly dusted in the proportion of 2 g/m².

Subsequently, 10 German cockroach adults (*Blattella germanica*) per group were liberated in the dish and allowed to come into contact with the dust for 30 minutes. After three days, more than 90% of the knocked down adults were killed.

EXAMPLE 10

Ten liters of water were placed in a 14-liter polypropylene bucket, and 1 g of each of the granular preparations formulated according to the Preparation Examples 14 and 15 was added thereto. After one day, about 100 full grown northern house mosquito larvae (*Culex pipiens pallens*) were liberated in the water. As the result, more than 90% of the larvae were killed within 24 hours.

EXAMPLE 11

Rice plants were grown up to the tillering stage in a 1/100,000 Wagner's pot and the water depth was kept at 5 cm. Each of the granular preparations formulated according to the Preparation Example 14 was applied thereto in the proportion of 10 kg per 10 ares. Thereafter, the pots were covered with a wire cage and smaller brown planthopper adults (*Laodelphax striatellus*) were liberated therein. After 24 hours, more than 90% of the adults were killed with each granular preparation.

EXAMPLE 12

Three grams of each of the oil sprays formulated according to the Preparation Example 2 were fogged, by means of an insect fogger (Burgess Vibrocrafters INC., U.S.A.), into a Peet Grady's chamber (the same as in Example 5) in which about 500 housefly adults (*Musca domestica*) had previously been liberated. After 30 minutes, more than 90% of the adults were knocked down.

EXAMPLE 13

Armyworms and cutworms, cabbage worm and diamond-back moth were artificially made parasitic on chinese cabbage which had been grown in a greenhouse. Then the house (2 m in height) was divided into spaces (30 m² in area, 2 m in height), and 10 g of each of the wettable powders formulated according to the Preparation Example 12 were fumigated by means of a thermofumigator (SEARCH) in each divided space. The spread of damage by the insects was hardly observed with any wettable powder.

EXAMPLE 14

Carmine mite female adults (*Tetranychus cinnabarinus*) were made parasitic on leaves of the potted kidney bean (2-leaves stage) which had elapsed 9 days after sowing, in a proportion of 10–15/leaf, and bred at 27°C for a week in a constant temperature room. Then numerous carmine mites were found to be bred at various growth stages. At this time, a 200-fold aqueous dilute solution of each emulsifiable concentrate formulated according to the Preparation Example 3 was sprayed in a proportion of 10 ml/pot on a turn table. After 10 days, damage to kidney beans by the insects was hardly observed.

What we claim is:

1. A compound of the formula (I),

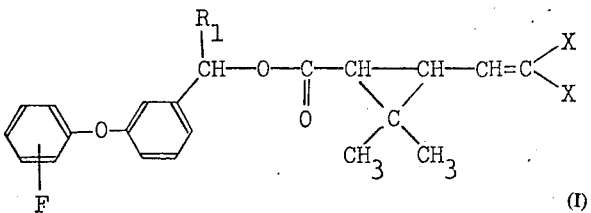

wherein $R_1$ is a hydrogen atom, a cyano or ethynyl group, and X is a chlorine, bromine or fluorine atom.

2.

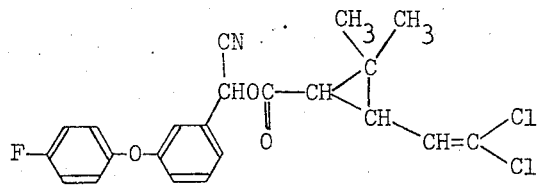

3.

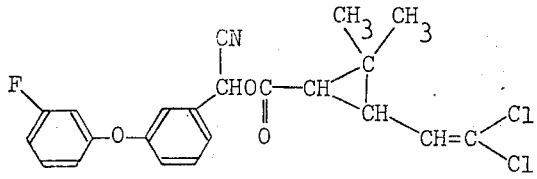

4.

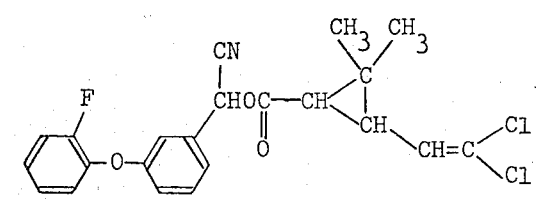

5. A composition comprising an inert carrier and as the active ingredient an effective amount of a compound of the formula,

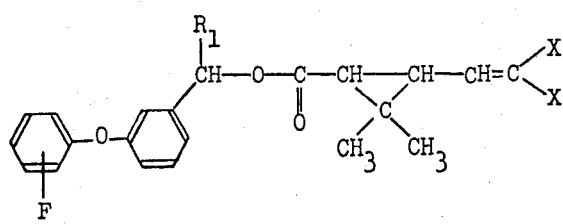

wherein $R_1$ is a hydrogen atom, a cyano or ethynyl group, and X is a chlorine, bromine or fluorine atom.

6. A composition according to claim 5, in the form of oil spray, emulsifiable concentrate, dusts, aerosol, wettable powder, granules, fine granules, mosquito coil, heating or non-heating fumigant, bait or thermal fogging agent.

7. A process for killing insects or mites, which comprises contacting the insects or mites with an effective amount of a compound as claimed in claim 1.

* * * * *